United States Patent [19]

Blacklock et al.

[11] Patent Number: 4,992,541
[45] Date of Patent: Feb. 12, 1991

[54] PROCESS FOR THE PREPARATION OF 1,1-DIOXO-7-SUBSTITUTED CEPHEMS

[75] Inventors: Thomas J. Blacklock, Clark, N.J.; John W. Butcher, Telford, Pa.; Paul Sohar, Warren, N.J.; Theresa Lamanec, Fajardo, P.R.

[73] Assignee: Merck & Co., Inc., Rahway, N.J.

[21] Appl. No.: 388,191

[22] Filed: Aug. 1, 1989

[51] Int. Cl.$^5$ .................. C07D 501/04; A61K 31/545
[52] U.S. Cl. .................... 540/221; 540/215; 540/230; 540/222
[58] Field of Search ............. 540/222, 221, 225, 230, 540/227, 215

[56] References Cited

U.S. PATENT DOCUMENTS 4,547,371 10/1985 Doherty et al. .................. 540/227

OTHER PUBLICATIONS

Schultz, H. S., J. Org. Chem. 1963, 28, 1140.
Fieser and Fieser, M. Reagents for Organic Synthesis, Wiley, New York 1967, p. 475.
Kahr, K. et al., C. Chem. Ber. 1960, 13, 132.
Blacklock, T. J., J. Org. Chem., 1989, 54, p. 3909 at Scheme 1.

Primary Examiner—Nicholas S. Rizzo
Attorney, Agent, or Firm—Curtis C. Panzer; Hesna J. Pfeiffer; Joseph F. DiPrima

[57] ABSTRACT

The present invention relates to an improved process for the preparation of the compounds of formula (I)

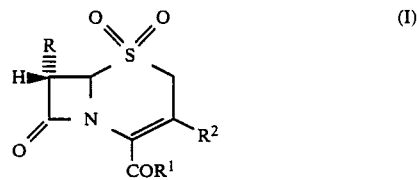

which involve the direct oxidation without N-protection of the compound of the formula (II)

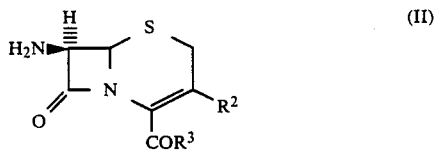

6 Claims, No Drawings

PROCESS FOR THE PREPARATION OF 1,1-DIOXO-7-SUBSTITUTED CEPHEMS

BACKGROUND OF THE INVENTION

U.S. Pat. No. 4,547,371 describes substituted cephalosporins containing sulfone moieties as potent elastase inhibitors which are useful anti-inflammatory/antidegenerative agents. Copending U.S patent application Ser. No. 930,193, filed Nov. 12, 1986 now abandoned also describes substituted cephalosporin sulfones as antiinflammatory and antidegenerative agents.

The compounds of this type are generally prepared from t-butyl 3-acetyloxymethyl-7β-amino-8-oxo-5-thia-l-azabicyclo [4.2.0]oct-2-ene-2-carboxylate (the t-butyl ester of 7-ACA) which is converted into the 7α-alkyoxy derivative via diazotization and displacement. It is this 7α-alkoxy derivative which is then oxidized to cephalosporins containing sulfone moieties. The procedure employed in Copending U.S patent application Ser. No. 930,193, filed Nov. 12, 1986 now abandoned involves the diazotization of 7-ACA t-butyl ester with p-toluenesulfonic acid/sodium nitrite in a biphasic methylene chloride/water system, followed by the rhodium acetate-catalyzed reaction with methanol to obtain, about 20-30% of the desired 7α-methoxy insertion product.

BRIEF DESCRIPTION OF THE INVENTION

The present invention relates to an improved process for the preparation of cephalosporins containing sulfone moieties which involve the direct oxidation of the compounds of the formula (II) without N-protection to afford the sulfone derivative which upon diazotization forms a unexpectedly stable intermediate that readily undergoes a displacement reaction with the appropriately substituted alcohols to afford key intermediates or the desired end products.

DETAILED DESCRIPTION OF THE INVENTION

The present invention relates to an improved process for the preparation of a compound of the formula (I)

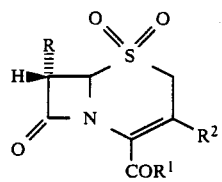

wherein:
R is
(1) $C_{1-6}$ alkoxy,
(2) $C_{2-6}$ alkenyloxy, or
(3) phenoxy;
$R^1$
(1) $C_{1-6}$ alkoxy,
(2) allyloxy,
(3) phenyl-$C_{1-6}$ alkoxy,
(4) $C_{1-6}$ alkoxycarbonyl-$C_{1-6}$ alkoxy,
(5) di($C_{1-6}$ alkyl)amino,
(6) $C_{1-6}$ alkoxycarbonyl-$C_{1-6}$ alkylamino,
(7) carboxypyrrolinyl,
(8) $C_{1-6}$ alkoxycarbonylpyrrolidinyl;
(9) allyloxycarbonylpyrrolidinyl;
$R^2$ is (1) $C_{1-6}$ alkyl or
(2) $C_{1-6}$ alkylcarbonyloxy-$C_{1-6}$ alkyl;
which comprises:
(A) oxidation of a compound of the formula (II)

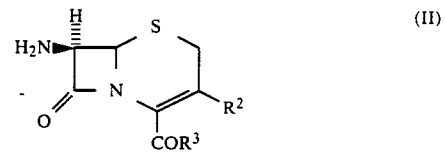

wherein $R^3$ is $C_{1-6}$ alkoxy, allyloxy, phenyl-$C_{1-6}$ alkoxy, or $C_{1-6}$ alkoxycarbonyl-$C_{1-6}$ alkoxy utilizing aqueous hydrogen peroxide and catalytic sodium tungstate to yield a compound of the formula (III)

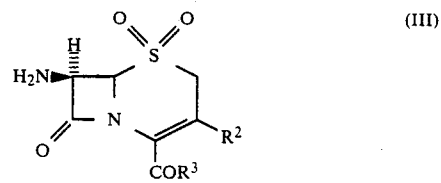

(B) diazotization of the compound of the formula (III) with standard diazotizing reagents and displacement of the diazo moiety with RH to give a compound of the formula (IV)

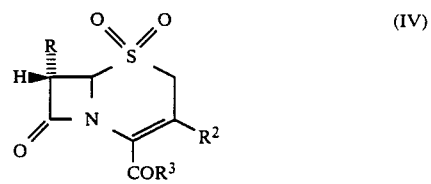

(C) where $R^1$ is other than $C_{1-6}$ alkoxy, allyloxy, phenyl-$C_{1-6}$ alkoxy, or $C_{1-6}$ alkoxycarbonyl-$C_{1-6}$ alkoxy, treatment of the compound of the formula (IV) wherein $R^3$ is t-butoxy with trifluoroacetic acid or wherein $R^3$ is allyloxy with $(Ph_3P)_4Pd$ and formic acid to afford a compound of the formula (V)

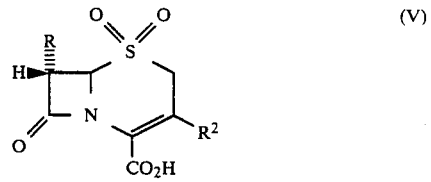

(D) conversion of the compound of the formula (V) to the corresponding acid halide and condensation with $R^1H$ to result in the compounds of the formula (I).

One embodiment of this invention is the process for the preparation of the compounds of the formula (I) wherein R is $C_{1-6}$ alkoxy. One class of this embodiment is the process for the preparation of these compounds in which $R^1$ is carboxypyrrolinyl, $C_{1-6}$ alkoxycarbonylpyrrolidinyl or allyloxycarbonylpyrrolidinyl; and $R^2$ is $C_{1-6}$ alkylcarbonyloxy-$C_{1-6}$ alkyl. Exemplifying this process is the preparation of 3-acetoxymethyl-7α-methoxy-8-oxo-5-thia-l-azabicyclo [4.2.0]-oct-2-ene-2-(2-(S)-carboxypyrrolidinocarboxamide)-5,5-dioxide.

A second embodiment of this invention is the process for the preparation of the compounds of the formula (III) which is the direct oxidation of the compounds of the formula (II) with aqueous hydrogen peroxide and catalytic sodium tungstate. Exemplifying this process is the preparation of t-butyl 3-acetoxymethyl-7β-amino-8-oxo-5-thia-1-azabicyclo [4.2.0]-oct-2-ene-2-carboxylate-5,5-dioxide.

The preparation of the starting material of the formula (II) wherein $R^3$ is t-butyl is accomplished in a manner analogous to the preparation of 7-ACA t-butyl ester which is described by Stedman [J. Med. Chem.. 1966, 9, 444] and involves the reaction of 3-substituted-7β-amino-8-oxo-5-thia-1azabicyclo[4.2.0]oct-2-ene-2-carboxylate and isobutylene in the presence of a strong acid catalyst, such as sulfuric acid. The esterification of the carboxylate moiety of 3-substituted-7β-amino-8-oxo-5-thia-l-azabicyclo [4.2.0]oct-2-ene-2-carboxylate with $C_{1-6}$ alkanols or substituted $C_{1-6}$ alkanols is accomplished under standard conditions.

The preparation of 3-substituted-7β-amino-8-oxo-5-thia-l-azabicyclo-[4.2.0]oct-2-ene-2-carboxylate-5,5-dioxide esters is accomplished via a direct oxidation of 3-substituted-7β-amino-8-oxo5-thia-l-azabicyclo[4.2.0]oct-2-ene-2-carboxylate ester, such as 7-ACA t-butyl ester, to the corresponding sulfone. Surprisingly, some of the anticipated problems due to the potential for N-oxidation of the 7-amino group are not encountered in this reaction. This direct oxidation without N-protection was ultimately effected with 30% aqueous hydrogen peroxide and catalytic sodium tungstate in ethyl acetate to give a high yield of the desired sulfone. However, some minor amount of N-oxidation occurred to form of a nearly insoluble byproduct which crystallized from the reaction medium.

The preparation of 3-substituted-7α-R-substituted-8-oxo-5-thia-l-azabicyclo-[4.2.0]oct-2-ene-2-carboxylate dioxide esters of the formula (IV) involves the conversion of the cis-or 7β-amino group to the 7α-R-substituent.

The diazotization of the sulfone analog of 3-substituted-7β-amino-8-oxo-5-thia-l-azabicyclo[4.2.0]oct-2-ene-2-carboxylate ester affords the corresponding diazosulfone which is orders-of-magnitude more stable in solution and is much less dependent on the purity of starting material than corresponding diazosulfide. Furthermore, these sulfone analogs are generated in near quantitative yield by homogeneous reaction with standard diazotizing reagents such as i-amyl nitrite or i-propyl nitrite (acid catalyzed).

The preparation of the compounds of formula (IV) involves a displacement of the diazo moiety with RH. For example, the rhodium-catalyzed insertion reactions with methanol using the diazosulfone, t-butyl 3-acetoxymethyl-7-diazo-8-oxo-5-thia-1-azabicyclo[4.2.0]-oct-2-ene-2-carboxylate-5,5-dioxide, shows a dramatic improvement in yield over the corresponding diazosulfide. The desired product identified as t-butyl 3-acetoxymethyl-7α-methoxy-8-oxo-5-thia-1-azabicyclo[4.2.0]-oct-2-ene-2- carboxylate-5,5-dioxide is formed in high yield. Similarly, the compounds of the formula (I) wherein $R^1$ is $C_{1-6}$ alkoxy, phenyl-$C_{1-6}$ alkoxy, allyloxy, or $C_{1-6}$ alkoxycarbonyl-$C_{1-6}$ alkoxy are prepared in an analogous manner. However, standard procedures of diazo insertion even when applied to the diazo sulfoxide gave low yield with poor isomeric ratio. In the instantly claimed invention, the use of polar medium and the minimal excess of alcohols or reagents surprisingly increased the yields significantly with the desired isomeric ratio greatly improved. The concentration of reagents and catalyst critical for the optimum results were achieved in a flow reactor on a preparative or larger scale.

The preparation of the compounds of the formula (I) where $R^1$ is other than $C_{1-6}$ alkoxy, phenyl-$C_{1-6}$ alkoxy, allyloxy, or $C_{1-6}$ alkoxycarbonyl-$C_{1-6}$ alkoxy, involves the formation of the compounds of the formula (V) via a deesterification of the compounds of the formula (IV) utilizing neat trifluoroacetic acid. The reaction is generally completed within 1–3 hours but slowed considerably if the starting material is predissolved in a nonreactive solvent, such as methylene chloride.

The carboxylate moiety is then converted into and acid halide group which is then condensed with an appropriately elaborated amine containing compound. The acid chloride is prepared from the corresponding acid by DMF-catalyzed reaction with oxalyl chloride in methylene chloride. A titration with base for total active hydrogens ($CF_3COOH$, $H_2O$, acid etc.) determines the initial charge of oxalyl chloride. The progress of acid chloride formation is monitored by gas evolution and confirmed by nmr. Incomplete reactions are charged with additional oxalyl chloride based on nmr assay. Acid chloride formation is nearly quantitative.

The acid chloride is rapidly added to a pre-cooled solution of excess anhydrous amine containing compound, such as proline t-butyl ester, or proline allyl ester and an organic amine, such as triethylamine, in an inert solvent, such as methylene chloride. The reaction is sensitive to moisture, temperature, and rate of addition of acid chloride. If necessary, deesterification of an the $C_{1-6}$ alkoxycarbonyl moiety with anhydrous trifluoroacetic acid in similar fashion to the deesterification of the compound of the formula (IV) affords the corresponding carboxy containing compound. Alternately, catalytic removal of the allyl group with $(Ph_3P)_4Pd$ and formic acid also affords the corresponding carboxy containing compound.

It was found that reaction of proline and excess isobutylene in methylene chloride using anhydrous benzenesulfonic acid in situ to effect phase transfer and N-protection of free proline (solubilization via protonation) afforded an 80% assay yield of proline t-butyl ester. This equilibrium reaction required three days to complete at 0°–5° C. at an optimized charge ratio of proline:benzenesulfonic acid:isobutylene of 1:1.5:12. A strongly basic workup neutralized the benzenesulfonate salts and freed the t-butyl ester for extraction into a neutral organic solvent. The product was typically used as a solution in methylene chloride or alternatively isolated in pure form by concentration and vacuum distillation.

The following examples illustrate the process of this invention and as such are not to be considered as limiting the invention set forth in the claims appended hereto.

EXAMPLE 1

The Preparation of 3-Acetoxymethyl-7α-methoxy-8-oxo-5-thia-l-azabicyclo [4.2.0]-oct-2-ene-2-(2-(S)-carboxypyrrolidinocarboxamide)-5.5-dioxide.

Step A: Preparation of t-Butyl 3-Acetoxymethyl-7β-amino-8-oxo-5-thia-l-azabicyclo[4.2.0]-oct-2-ene-2-carboxylate To a 12L round-bottomed flask was charged under nitrogen a slurry of 3-acetyloxymethyl-7β-amino-8- oxo-5-thia-1-azabicyclo[4.2.0]oct-2-ene -2-carboxylic acid (7-ACA, 436 g, 1.6 mole) in anhydrous 1,2-dimethoxyethane (DME, 4.0L). The slurry was cooled to 5° C. and was maintained at ≦15° C. as conc. sulfuric acid (400 mL, 7.5 mole) was slowly added. The mixture, now homogeneous, was further cooled to 4°-6° C. and was maintained near 5° C. throughout the period when liquefied isobutylene (3.0L, 32 mole) was slowly added subsurface over about 2 hours via a diptube. When the reaction was deemed complete, the batch was slowly quenched into a well-stirred mixture of saturated aqueous sodium bicarbonate (14.0L, 16.7 mole) and isopropyl acetate (4.0L) at 5° C. Vigorous evolution of $CO_2$ occurred. The biphasic mixture was stirred for 10 minutes, after which the layers were allowed to separate. The lower aqueous layer was removed and reextracted with isopropyl acetate (2×4.0L). The combined isopropyl acetate extracts were dried over sodium sulfate (500 g), filtered, and assayed for product by HPLC. The product solution was concentrated under vacuum at ≦25° C. to 1.1L. Crystallization of the product ensued near the end of the concentration. At this point hexanes (4.1L) was slowly added to the stirred product mixture. The batch was aged for 2 hours, cooled to 0°-5° C. and aged for an additional 2-4 hours. The product was filtered, washed with hexanes (1L), and dried in vacuo at 40° C. to constant weight.

Step B: Preparation of t-Butyl 3-Acetoxymethyl-7β-amino-8-oxo-5-thia-1-azabicyclo [4.2.0]-oct-2-ene-2-carboxylate-5.5-dioxide In a 4L three-necked round-bottomed flask was dissolved the compound from Example 1 Step A (100 assay g, 0.305 mole) in ethyl acetate (2.0L) at 25° C. The solution was stirred rapidly as solid sodium tungstate dehydrate (10.0 g, 0.0305 mole) and 30% hydrogen peroxide (125 mL, 1.22 mole) were added. The temperature of this now biphasic mixture was maintained at 20°-25° C. with cooling water for 2 hours. After 2 hours, an additional charge of 30% hydrogen peroxide (25 mL, 0.25 mole) was made and the batch was aged until substantially complete (10-18 hours). After reaction completion the mixture was diluted with ethyl acetate (3L) and cooled to 10° C. The reaction mixture was stirred well while a solution of sodium sulfite (100 g, 0.8 mole) in water (2.0L) was slowly added to decompose any remaining hydrogen peroxide. The biphasic mixture was further cooled to 5° C. and a cold (5° C.) solution of aqueous sodium carbonate (2.0L, 0.153M, 0.306 moles) was slowly added to decompose oxime byproduct. The mixture was stirred for 10 minutes. Stirring was discontinued and the layers were allowed to separate (15 min). The lower aqueous layer was removed and discarded. The upper ethyl acetate product layer was then washed with saturated sodium chloride (1L). The upper ethyl acetate layer was dried over sodium sulfate (100 g), filtered, and the cake washed with ethyl acetate (1.0L). The combined filtrate and wash was assayed by HPLC to contain amino sulfone. The batch was concentrated under vacuum at ≦30° C. to 900 mL. Crystallization occurred during concentration. Hexanes (1.6L) was slowly added to the stirred product slurry and the batch was aged with stirring for 2 hours at 20°-25° C. and 2 hours at 0°-5° C. The product was filtered and rinsed with hexanes (500 mL), and dried in vacuo at 30° C. to constant weight.

Step C: Preparation of t-Butyl 3-Acetoxymethyl-7α-methoxy-8-oxo-5-thia-1-azabicyclo- [4.2.01]-oct-2-ene-2-carboxylate-5.5-dioxide A 2-L 3-necked round-bottomed flask equipped with a mechanical agitator and nitrogen bubbler was charged with the compound of Example 1 Step B (75.0 g, 0.208 mole) in ethyl acetate (750 mL). Isopropyl nitrite (24.1 assay g, 0.271 mole, 25-50 wt. % in methylene chloride) was added to the stirred solution at 15°-20° C. followed by a catalytic amount of trifluoroacetic acid (0.1 mL, 0.005 mole). The batch temperature rose to 31° C. over 15 minutes and was monitored by HPLC for completeness. The reaction normally completes within 1 hour as judged by HPLC. When diazotization was complete the batch was diluted with ethyl acetate (750 mL) and concentrated in vacuo at ≦30° C. to approximately 750 mL. To avoid possible explosion caused by concentration of the diazo product, it is important that product does not crystallize near the neck of the flask during concentration. The batch was then filtered, if necessary, to remove insolubles and subsequently diluted to exactly 10L with fresh ethyl acetate (approximately 250 mL). The mixture was then transferred to a cooled 2L reaction kettle and was cooled to −5° C. and vacuum-purged three times with nitrogen. Simultaneous to preparation of the diazocephalosporanate above, rhodium octanoate dimer (1.5 g, 385 mmole) was dissolved in methanol (128 mL) and diluted to 1L with ethyl acetate (850 mL). The mixture was transferred to a Jacketed and externally cooled 2-L reaction kettle equipped with an overhead mechanical agitator, vacuum/nitrogen purger control, and bottom outlet valve. The stirred mixture was cooled to −5° C. and vacuum purged three times with nitrogen. Prior to reaction with the diazocephalosporanate, triethylamine (3 mL) was added to the catalyst mixture and the solution was stirred for 5 minutes. The solutions of catalyst and diazocephalosporanate were then transferred at a rate of 175 mL/min from the bottom outlet valves of the reaction kettles through a (0.5 cm×40 cm) Kenics static flow reactor (¼-40-174-0) which exited into a stirred open 4L flask. As the above reaction rapidly eliminates about 4.7L of nitrogen gas, it must not be run in a closed vessel. The batch was then stirred for 5 minutes to allow any remaining diazo compound to react and was then neutralized with acetic acid (10 mL, 0.175 mole). The batch was then concentrated in vacuo to approximately 1.0L, first washed with deionized water (600 mL) containing NaCl (60 g) and $H_3PO_4$ (85% 1.7 mL), and secondly with a solution of 10% sodium chloride (300 mL). The ethyl acetate layer was dried over $Na_2SO_4$ (200 g), and then passed through a bed of silica gel (0.5 kg). The silica gel was then washed with ethyl acetate (about 3L) until >99% of the product had been recovered as determined by HPLC assay. The batch and wash were combined and concentrated in vacuo at <30° C. to 400 mL. Hexanes (400 mL) was slowly added, during which crystallization occurred. The batch was further concentrated to 200 mL and diluted with hexanes (1.2L) over 4 hours. The batch was aged with stirring for 4 hours at 25° C. and then 24 hours at 0-5° C. The batch was filtered and the cake washed with 300 mls of hexanes. The cake was dried in vacuo ≦40° C.

Step D: Preparation of 3-Acetyloxymethyl-7α-methoxy-8-oxo-5-thia-1-azabicyclo [4.2.0]oct2-ene-2-(2-(S)-t-butyloxycarbonylpyrrolidinecarboxamide)-5,5-dioxide Trifluoroacetic acid (200 mL, 296 g, 2.60, mole) was charged neat under a dry nitrogen atmosphere to a 1L, 3-necked, round-bottomed flask. The neat acid was cooled to 10.C and the compound of Example 1 Step C (50.0 assay g, 0.133 mole) was charged portionwise through an addition funnel at such a rate to avoid globbing and to maintain a reaction temperature of 20°-25° C. The temperature was kept at 20°-25° C. and the reaction was maintained dry under nitrogen atmosphere while monitored by HPLC until complete. Upon completion, the reaction mixture was concentrated under high vacuum (20 mm Hg) at ≦30° C. to a volume of 60 mL. The mixture was diluted with methylene chloride (100 mL) and concentration was resumed under low vacuum (250 mm Hg) at 20°-25° C. until a volume of 60 mL was attained. This flushing procedure, addition of methylene chloride (100 mL) followed by a low-vacuum concentration to 60 mL, was repeated until a base titration on the batch indicated a ≦1.5:1 molar ratio of strong acid (trifluoroacetic acid):weak acid (3-acetyloxymethyl-7α-methoxy-8-oxo-5-thia-1-azabicyclo[4.2.0]oct-2-ene-2-carboxylic acid 5,5-dioxide). Under carefully maintained dry condition, the batch containing approximately 42.5 g of this weak acid was then diluted to exactly 450 mL with methylene chloride (about 400 mL). A catalytic amount of dimethylformamide (0.4 mL, 0.005 mole) was added, the mixture stirred well. The mixture was cooled to 15° C. and maintained at 15°-20° C. as oxalyl chloride (25.6 mL, 38.1 g, 0.294 mole corr. for 98% purity) was added dropwise over 15 min. The reaction was then aged at 15°-20° C. Upon completion, the batch was concentrated under vacuum at ≦25° C. to a volume of 200 mL. Methylene chloride (K.F.≦0.05, 200 mL) was added and concentration was continued to a volume of 200 mL. This flushing procedure was repeated two times (2×200 mL) and was followed by a final dilution of the batch to a volume of 360 mL with methylene chloride (about 160 mL) to give the desired acid chloride. A solution of t-butyl prolinate (32.0 assay g, 0.187 mole) which was prepared according to Example 2 in dry methylene chloride (K.F. ≦0.05, 400 mL) was charged to a dry 3-necked 2L round-bottom flask equipped with an overhead mechanical stirrer, thermometer, and nitrogen atmosphere bubbler. The mixture was cooled to 0° C. and maintained at 0°-2° C. with moderate stirring as triethylamine (26 mL, 18.9 g, 0.187 mole) was slowly added. The batch was then further cooled to −15° C. and the agitation increased. With full external cooling, the cold (−15° C.) solution of acid chloride from above was then added to the proline t-butyl ester solution as rapidly as possible (≦15 min) allowing the batch temperature to attain a maximum temperature of 25° C. After addition, the batch was stirred for 15 minutes and then washed two times with cold (5° C. aqueous phosphoric acid (1% v/v, 2×225 mL) and two times with cold (5° C.) potassium phosphate (monobasic, 1% w/v, 2×225 mL). The methylene chloride product layer was dried over sodium sulfate (500 g) and assayed by HPLC which indicated the presence of the desired product. This material was used in the subsequent step without further purification.

Step E: Preparation of 3-Acetyloxymethyl-7α-methoxy-8-oxo-5-thia-1-azabicyclo[4.2.0]oct 2-ene-2-(2-(S)-carboxypyrrolidinecarboxamide)-5,5-dioxide A solution of the compound of Example 1 Step D (54.2 assay g, 0.115 mole) in methylene chloride was concentrated under vacuum at ≦30° C. to a thick oil/foam. The reaction mixture was placed under nitrogen and the vessel was externally cooled to 0°-5° C. With slow agitation of the thick mass, trifluoroacetic acid (200 mL, 2.6 mole) was added in one portion. A mild exotherm occurred raising the temperature of the batch to 20° C. The resulting homogeneous solution was then stirred at 20°-25° C. until deprotection was complete as judged by HPLC (1-4 hrs). The reaction mixture was then concentrated under vacuum at ≦30° C. to about 75 mL. Ethyl acetate (200 mL) was added and concentration was resumed until a volume of approximately 75 mL was attained. This flushing procedure (each time adding 200 mL ethyl acetate followed by vacuum concentration to 75 mL) was repeated until a base titration on a 1 mL aliquot of the batch revealed a ≦2:1 molar ratio of strong acid (trifluoroacetic acid $pK_a=2.1$) to weak acid (the desired product $pK_a=5.6$). The crude product solution was then adjusted to a volume of 100 mL and used immediately in the next step. The ethyl acetate product solution from above containing the desired product (about 47.3 assay g, 0.114 mole) was charged onto a 5 cm×60 cm column of silica gel (380 g, 8-9 g Silica gel/g product) slurry-packed in ethyl acetate. The column was eluted with ethyl acetate and the eluate monitored by HPLC for product. A product rich cut of approximately 2L beginning after about 1 bv (bed-volume) was collected. The rich cut was concentrated under vacuum at ≦30° C. to a volume of 160 mL and seeded. The crystallizing mixture was aged with stirring for 12-18 hrs at 25° C. and followed by 24 hrs age at 0°-5° C. The product was filtered, washed with cold ethyl acetate (40 mL), dried under a stream of dry nitrogen, and further dried under vacuum at 40° C. to afford crystalline 3-acetyloxymethyl-7α-methoxy-8-oxo-5-thia-1-azabicyclo [4.2.0]oct-2-ene-2-(2-(S)-carboxypyrrolidinecarboxamide)-5,5-dioxide. The desired product (40.0 g, 0.096 mole) was slurried in ethyl acetate (1.0L) and heated at reflux until a clear solution was obtained. Darco KB (10 g) was slowly added and the hot solution (>60° C.) aged for 30 min. The solution was filtered and the darco KB cake washed with hot ethyl acetate (100 mL). The combined filtrate and wash was concentrated under vacuum at ≦50° C. to a final volume of 280 mL (7.0 mL/g). The crystallizing mixture was allowed to cool, aged for 12 hr at 20°-25° C. followed by 24 hr at 0°-5° C. The product was filtered, the filter cake washed with cold ethyl acetate (5° C., 20 mL), dried with dry nitrogen, and further dried to constant weight under vacuum at 80° C. M.P. - 160°-161° C. (dec)

| Microanalysis | | Calc. | Found |
|---|---|---|---|
| | N | 6.73 | 6.67 |
| | C | 46.15 | 46.50 |
| | H | 4.84 | 4.78 |
| | S | 7.70 | 7.74 |

EXAMPLE 2

Preparation of t-Butyl L-prolinate

To a 12L round-bottomed flask fitted with a mechanical stirrer, high efficiency reflux condenser ($\leq -10°$ C.), adjustable diptube inlet, and overhead nitrogen bubbler was charged a slurry of L-proline (600 g, 5.22 mole) in methylene chloride (6.0L, K.F.$\leq 0.01\%$). The slurry was cooled to 5° C. and maintained at <20° C. as benzenesulfonic acid (1.24 kg, 7.83 mole) was slowly added. The reaction mixture, now homogeneous, was further cooled under nitrogen to 0°–5° C. and liquefied isobutylene (5.86L, 67.8 mole) was added subsurface via the diptube over 2 hours. The batch was then aged for 3 days at 5° C. under nitrogen. Upon completion, the batch was slowly quenched under nitrogen into well-stirred cold (0°–5° C.) aqueous sodium hydroxide (15.6L, 1.0 molar, 15.6 moles). The biphasic mixture was stirred for 10 minutes after which, the layers were allowed to separate. The pH of the aqueous layer measured 12–13. The lower methylene chloride layer was removed and set aside. The upper aqueous layer was then reextracted with methylene chloride (2×2.0L). The methylene chloride extracts were combined and concentrated under vacuum at $\leq 25°$ C. to a volume of 6.0L. The batch was then washed with aqueous sodium hydroxide (2×4.0L, 0.3 molar, 2.4 moles). The aqueous wash layers were combined and subsequently extracted with methylene chloride (2L). The methylene chloride extracts were then combined, dried over sodium sulfate (500 g), filtered, and concentrated under vacuum at $\leq 25°$ C. to about 1.5L (cf.50% soln K.F.$\leq 0.06\%$). The batch was stored cold (0°–5° C.) under nitrogen. The concentrated product must be kept at 0°–5° C. to avoid exothermic decomposition.

EXAMPLES 3–10

Utilizing the general procedures from Example 1 and substituting the appropriate reactants the following compounds of the formula (I) are prepared.

| Compound # | R | $R^1$ | $R^2$ |
|---|---|---|---|
| 3 | CH$_3$O | (CH$_3$)$_3$CO | CH$_3$ |
| 4 | PhO | CH$_3$O | CH$_3$ |
| 5 | CH$_2$=CHCH$_2$O | CH$_3$O | CH$_3$ |
| 6 | CH$_3$O | (CH$_3$)$_2$NH | CH$_2$OAc |
| 7 | PhO | CH$_3$-L-Pro | CH$_2$OAc |
| 8 | CH$_2$=CHCH$_2$O | CH$_3$COCH$_2$NH | CH$_3$ |
| 9 | CH$_3$O | L-Pro | CH$_3$ |
| 10 | PhO | t-Bu-L-Pro | CH$_2$OAc |
| 11 | CH$_3$O | Allyl-L-Pro | CH$_2$OAc |

L-Pro = L-prolinyl

What is claimed is:

1. A process for the preparation of a compound of the formula (I)

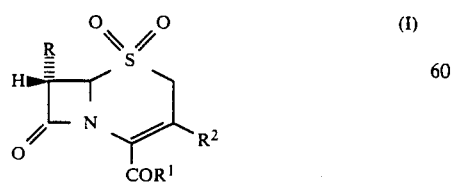

(I)

wherein:
R is
(1) C$_{1-6}$ alkoxy,
(2) C$_{2-6}$ alkenyloxy, or
(3) phenoxy;
R$^1$ is
(1) C$_{1-6}$ alkoxy,
(2) allyloxy,
(3) phenyl-C$_{1-6}$ alkoxy,
(4) C$_{1-6}$ alkoxycarbonyl-C$_{1-6}$ alkoxy,
(5) di(C$_{1-6}$ alkyl)amino,
(6) C$_{1-6}$ alkoxycarbonyl-C$_{1-6}$ alkylamino,
(7) carboxypyrrolinyl,
(8) C$_{1-6}$ alkoxycarbonylpyrrolidinyl, or
(9) allyloxycarbonylpyrrolidinyl;
R$^2$ is
(1) C$_{1-6}$ alkyl or
(2) C$_{1-6}$ alkylcarbonyloxy-C$_{1-6}$ alkyl;
which comprises:
(A) oxidation of a compound of the formula (II)

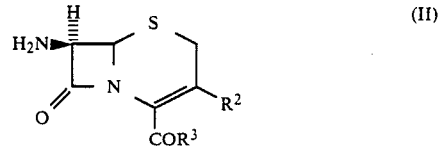

(II)

wherein R$^3$ is C$_{1-6}$ alkoxy, phenyl-C$_{1-6}$ alkoxy, allyloxy, or C$_{1-6}$ alkoxycarbonyl-C$_{1-6}$ alkoxy utilizing aqueous hydrogen peroxide and catalytic sodium tungstate to yield a compound of the formula (III)

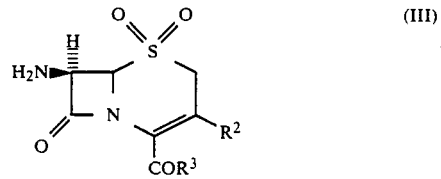

(III)

(B) diazotization of the compound of the formula (III) with standard diazotizing reagents and displacement of the diazo moiety with RH to give a compound of the formula (IV)

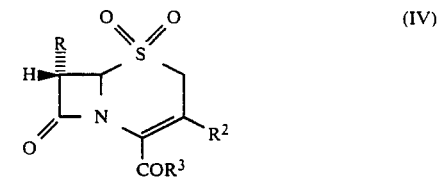

(IV)

(C) where R$^1$ is other than C$_{1-6}$ alkoxy, phenyl-C$_{1-6}$ alkoxy, allyloxy, or C$_{1-6}$ alkoxycarbonyl-C$_{1-6}$ alkoxy, treatment of the compound of the formula (IV) wherein R$^3$ is t-butoxy with trifluoroacetic acid or wherein R$^3$ is allyloxy with (Ph$_3$P)$_4$Pd and formic acid to afford a compound of the formula (V)

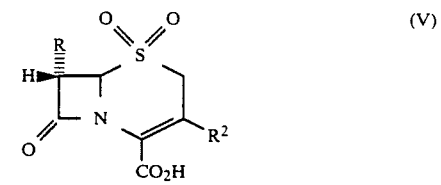

(V)

(D) conversion of the compound of the formula (V) to the corresponding acid halide and condensation with $R^1H$ to result in the compounds of the formula (I).

2. A process according to claim 1 wherein R is $C_{1-6}$ alkoxy.

3. A process according to claim 2 wherein:

$R^1$ is carboxypyrrolinyl, $C_{1-6}$ alkoxycarbonylpyrrolidinyl or allyloxycarbonylpyrrolidinyl; and $R^2$ is $C_{1-6}$ alkylcarbonyloxy-$C_{1-6}$ alkyl.

4. A process according to claim 3 for the preparation of 3-acetoxymethyl-7a-methoxy-8-oxo-5-thia-1-azabicyclo [4.2.0]-oct-2-ene-2-(2-(S)-carboxypyrrolidinocarboxamide)-5,5-dioxide.

5. A process for the preparation of the compounds of the formula (III)

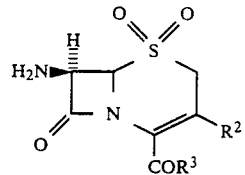

wherein:
$R^2$ is
   (1) $C_{1-6}$ alkyl or
   (2) $C_{1-6}$ alkylcarbonyloxy-$C_{1-6}$ alkyl;
$R^3$ is
   (1) $C_{1-6}$ alkoxy,
   (2) allyloxy
   (3) phenyl-$C_{1-6}$ alkoxy, or
   (4) $C_{1-6}$ alkoxycarbonyl-$C_{1-6}$ alkoxy;
which comprises:
(A) oxidation of a compound of the formula (II)

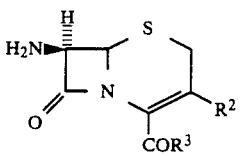

utilizing aqueous hydrogen peroxide and catalytic sodium tungstate.

6. A process according to claim 5 which is the process for the preparation of t-butyl 3-acetoxymethyl-7β-amino-8-oxo-5-thia-l-azabicyclo-[4.2.0]-oct-2-ene-2-carboxylate-5,5-dioxide.

* * * * *